(12) United States Patent
Watanabe et al.

(10) Patent No.: US 11,852,607 B2
(45) Date of Patent: Dec. 26, 2023

(54) SENSOR ELEMENT AND GAS SENSOR

(71) Applicant: NGK INSULATORS, LTD., Aichi (JP)

(72) Inventors: Yusuke Watanabe, Nagoya (JP); Shotaro Niizuma, Kasugai (JP)

(73) Assignee: NGK INSULATORS, LTD., Nagoya (JP)

( * ) Notice: Subject to any disclaimer, the term of this patent is extended or adjusted under 35 U.S.C. 154(b) by 147 days.

(21) Appl. No.: 17/205,633

(22) Filed: Mar. 18, 2021

(65) Prior Publication Data
US 2021/0302364 A1 Sep. 30, 2021

(30) Foreign Application Priority Data

Mar. 27, 2020 (JP) .................... 2020-058666

(51) Int. Cl.
*G01N 27/04* (2006.01)
*G01N 27/406* (2006.01)
*G01N 27/41* (2006.01)
*G01N 33/00* (2006.01)

(52) U.S. Cl.
CPC ......... *G01N 27/41* (2013.01); *G01N 27/4062* (2013.01); *G01N 33/0037* (2013.01)

(58) Field of Classification Search
CPC ........... G01N 27/41; G01N 27/04–205; G01N 27/4062; G01N 27/4065; G01N 27/4071; G01N 27/4076
See application file for complete search history.

(56) References Cited

U.S. PATENT DOCUMENTS

| | | | |
|---|---|---|---|
| 2001/0008211 A1* | 7/2001 | Kato | G01N 27/4074 204/429 |
| 2014/0042025 A1 | 2/2014 | Furuta | |
| 2018/0067073 A1* | 3/2018 | Tomimatsu | H03H 17/0009 |
| 2018/0126334 A1* | 5/2018 | Nakano | F01N 3/0814 |
| 2018/0172622 A1* | 6/2018 | Furuta | G01N 27/4067 |
| 2019/0011395 A1* | 1/2019 | Miyamoto | G01N 27/4071 |

FOREIGN PATENT DOCUMENTS

| | | | | |
|---|---|---|---|---|
| DE | 102016202218 A1 * | 8/2016 | | G01N 27/4071 |
| JP | 2014-052363 A | 3/2014 | | |
| JP | 2018-100961 A | 6/2018 | | |

* cited by examiner

*Primary Examiner* — Joshua L Allen
*Assistant Examiner* — Vivian A Tran
(74) *Attorney, Agent, or Firm* — Mattingly & Malur, PC

(57) ABSTRACT

A sensor element includes a first pump cell including a first pump electrode and a first reference electrode, a first pump circuit including the first pump cell and a first reference electrode lead, a second pump cell including a second pump electrode and a second reference electrode and a second pump circuit including the second pump cell and a second pump electrode. A resistance value R2 of the second pump circuit is higher than a resistance value R1 of the first pump circuit, and a porosity P2 of the second reference electrode lead is higher than a porosity P1 of the first reference electrode lead.

4 Claims, 5 Drawing Sheets

SENSOR ELEMENT AND GAS SENSOR

The application claims priority to Japanese Patent Application No. 2020-058666 filed in the Japan Patent Office on Mar. 27, 2020, the entire contents of which are incorporated herein by reference.

BACKGROUND OF THE INVENTION

1. Field of the Invention

The present invention relates to a sensor element and a gas sensor.

2. Description of the Related Art

Sensor elements are known in the related art for detecting a specific gas concentration such as a NOx concentration in a measurement-object gas such as an exhaust gas of an automobile (e.g., PTLs 1 and 2). PTL 1 describes a sensor element including an element body including solid electrolyte layers, a first measurement chamber and a second measurement chamber disposed inside the element body, a detection electrode disposed in the first measurement chamber, a pumping electrode disposed in the second measurement chamber, a reference oxygen chamber disposed inside the element body, and a reference electrode and a pumping electrode disposed in the reference oxygen chamber. It is also described that a current is caused to flow between the detection electrode and the reference electrode to feed oxygen into the reference oxygen chamber, and that a current is caused to flow between the pumping electrode in the second measurement chamber and the pumping electrode in the reference oxygen chamber to feed oxygen into the reference oxygen chamber. PTL 2 describes that a lead connected to a reference electrode has gas permeability to degas oxygen stored in the reference electrode. Accordingly, it is possible to prevent oxygen from being excessively stored in the reference electrode.

CITATION LIST

Patent Literature

PTL 1: JP 2018-100961 A
PTL 2: JP 2014-052363 A

SUMMARY OF THE INVENTION

As in PTL 1, when a plurality of electrodes are located in the reference oxygen chamber, there are leads, each of which is connected to one of the electrodes. In this case, it is conceivable that the plurality of leads have gas permeability to suppress an increase in oxygen concentration in the reference oxygen chamber. However, how the porosities of the plurality of leads are to be set has not been sufficiently studied. For example, when the leads have high porosities, an increase in manufacturing variations in the resistance values of the leads may cause an increase in manufacturing variations in the resistance values of circuits including the leads. However, such a case has not been taken into consideration.

The present invention has been made to solve such a problem, and a main object of the present invention is to provide a sensor element with small manufacturing variations while suppressing an increase in oxygen concentration in a reference gas chamber.

To achieve the main object described above, the present invention is configured as follows.

A sensor element according to the present invention is a sensor element for detecting a specific gas concentration in a measurement-object gas, the sensor element includes:

an element body including an oxygen-ion-conductive solid electrolyte layer and having formed therein a measurement-object gas flow section and a reference gas chamber, the measurement-object gas flow section being a section into and through which the measurement-object gas is introduced and flows, the reference gas chamber being a chamber in which a reference gas used as a reference to detect the specific gas concentration in the measurement-object gas is to be stored;

a first pump cell including a first pump electrode disposed in a portion of the element body that comes into contact with the measurement-object gas, and a first reference electrode that is porous and disposed in the reference gas chamber, the first pump cell being configured to pump oxygen into around the first reference electrode from around the first pump electrode;

a first pump circuit including the first pump cell, a first pump electrode terminal disposed on an outer side of the element body, a first reference electrode terminal disposed on the outer side of the element body, a first pump electrode lead that connects the first pump electrode terminal and the first pump electrode to each other, and a first reference electrode lead that connects the first reference electrode terminal and the first reference electrode to each other;

a second pump cell including a second pump electrode disposed in a portion of the element body that comes into contact with the measurement-object gas, and a second reference electrode that is porous and disposed in the reference gas chamber, the second pump cell being configured to pump oxygen into around the second reference electrode from around the second pump electrode; and a second pump circuit including the second pump cell, a second pump electrode terminal disposed on the outer side of the element body, a second reference electrode terminal disposed on the outer side of the element body, a second pump electrode lead that connects the second pump electrode terminal and the second pump electrode to each other, and a second reference electrode lead that connects the second reference electrode terminal and the second reference electrode to each other, wherein a resistance value R2 between the second pump electrode terminal and the second reference electrode terminal of the second pump circuit is higher than a resistance value R1 between the first pump electrode terminal and the first reference electrode terminal of the first pump circuit, and a porosity P2 of the second reference electrode lead is higher than a porosity P1 of the first reference electrode lead.

In the sensor element, the second porous reference electrode lead is connected to the second porous reference electrode. Accordingly, oxygen pumped into the reference gas chamber by the first and second pump cells can be released to outside the sensor element through pores in the second reference electrode lead. This can suppress an increase in oxygen concentration in the reference gas chamber. In addition, the second reference electrode lead of the second pump circuit having a higher resistance value among the first and second pump circuits has a higher porosity than the first reference electrode lead of the first pump circuit having a lower resistance value. The higher the porosity of a lead, the more likely it is that the resistance value of the lead varies due to a manufacturing error. In the sensor element according to the present invention, however, the porosity P2 of the second reference electrode lead, which is a lead included in a circuit having a higher total resistance value among the first and second pump circuits, is set to be high. Thus, even if the resistance value of the second reference electrode lead varies for each sensor element, the influence on the resistance value R2, that is, the variation in the resistance value R2, is relatively small. In contrast, if the porosity P1 of the first reference electrode lead is set to be high, the resistance value of the first reference electrode lead varies for each sensor element. As a result, the influence on the resistance value R1, that is, the variation in the resistance value R1, is relatively large. In the sensor element according to the present invention, accordingly, for example, as compared with the case where the porosity P1 is set to be greater than or equal to the porosity P2, individual differences for the manufacturing of a plurality of sensor elements are small, that is, manufacturing variations are small. Therefore, the sensor element according to the present invention can reduce manufacturing variations while suppressing an increase in oxygen concentration in the reference gas chamber.

In the sensor element according to the present invention, the porosity P2 may be greater than or equal to 5% and less than or equal to 25%. When the porosity P2 is greater than or equal to 5%, the effect of suppressing an increase in oxygen concentration in the reference gas chamber is more reliably obtained. When the porosity P2 is less than or equal to 25%, a break in the lead at the manufacturing time can be suppressed.

In the sensor element according to the present invention, the porosity P1 may be greater than or equal to 1% and less than or equal to 5%.

A gas sensor according to the present invention includes the sensor element having any of the configurations described above. The gas sensor can obtain effects similar to those of the sensor element according to the present invention described above, for example, the effect of reducing manufacturing variations while suppressing an increase in oxygen concentration in the reference gas chamber.

DETAILED DESCRIPTION OF THE INVENTION

Figure 1:
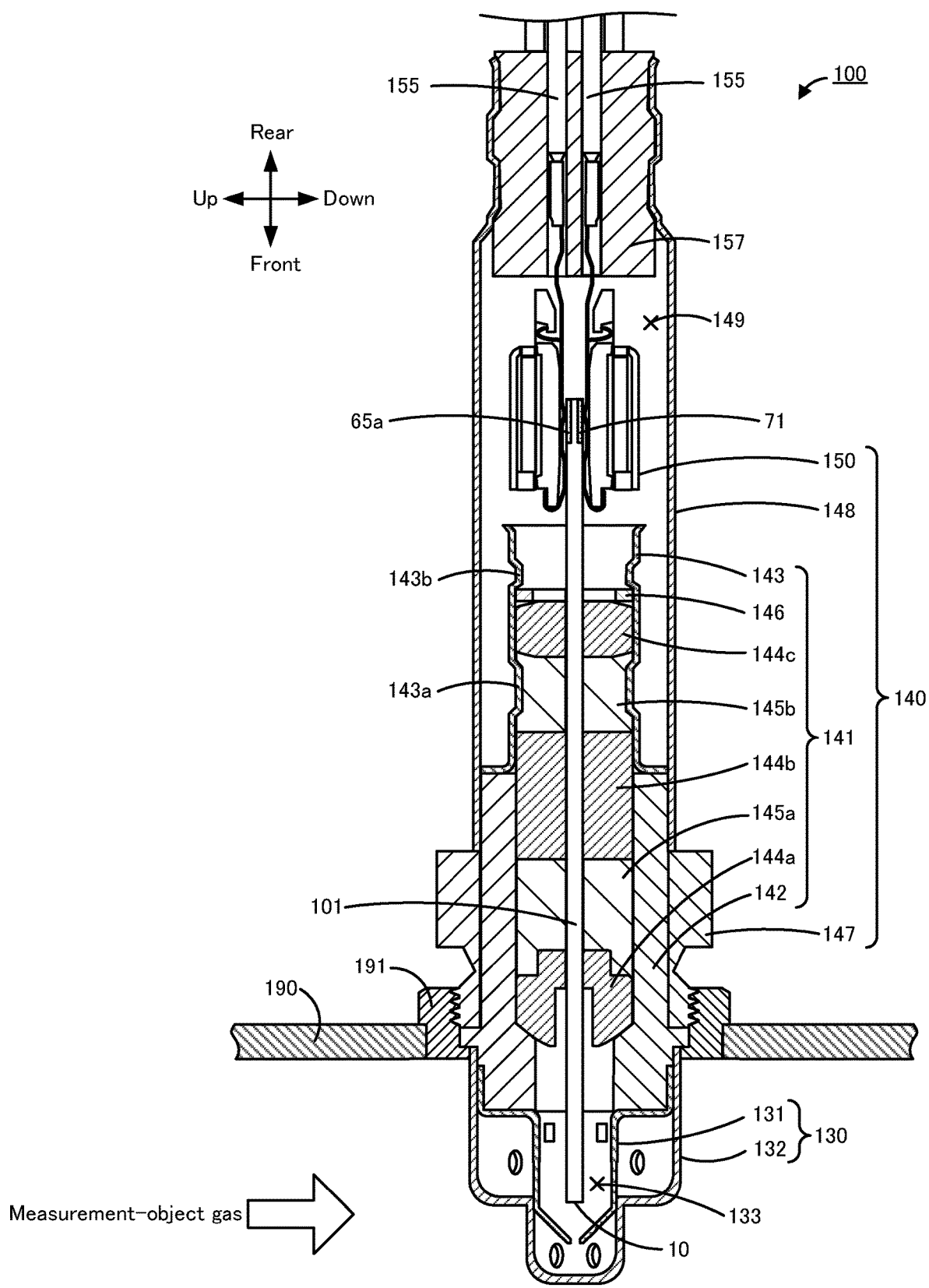
FIG. 1 is a longitudinal sectional view of a gas sensor 100.
Figure 2:
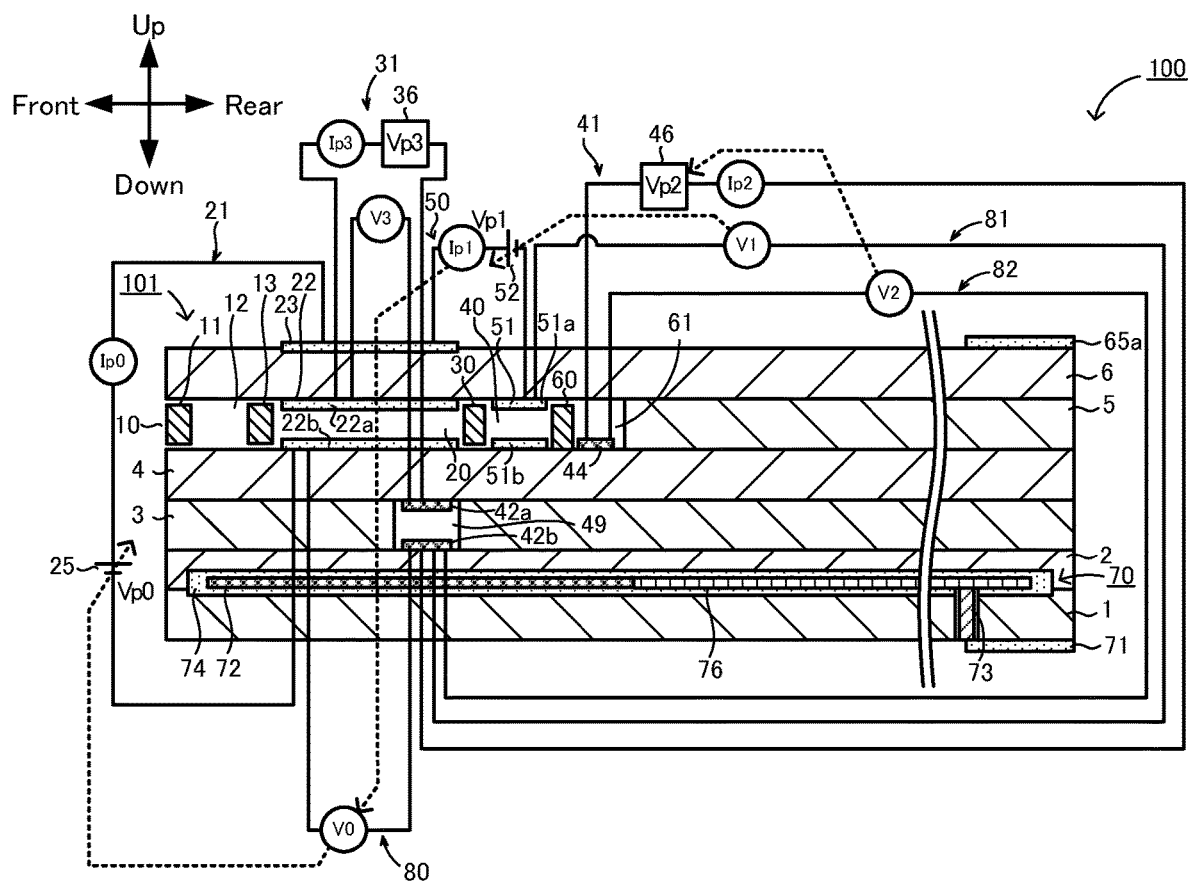
FIG. 2 is a schematic sectional view schematically illustrating an example configuration of a sensor element 101.
Figure 3:
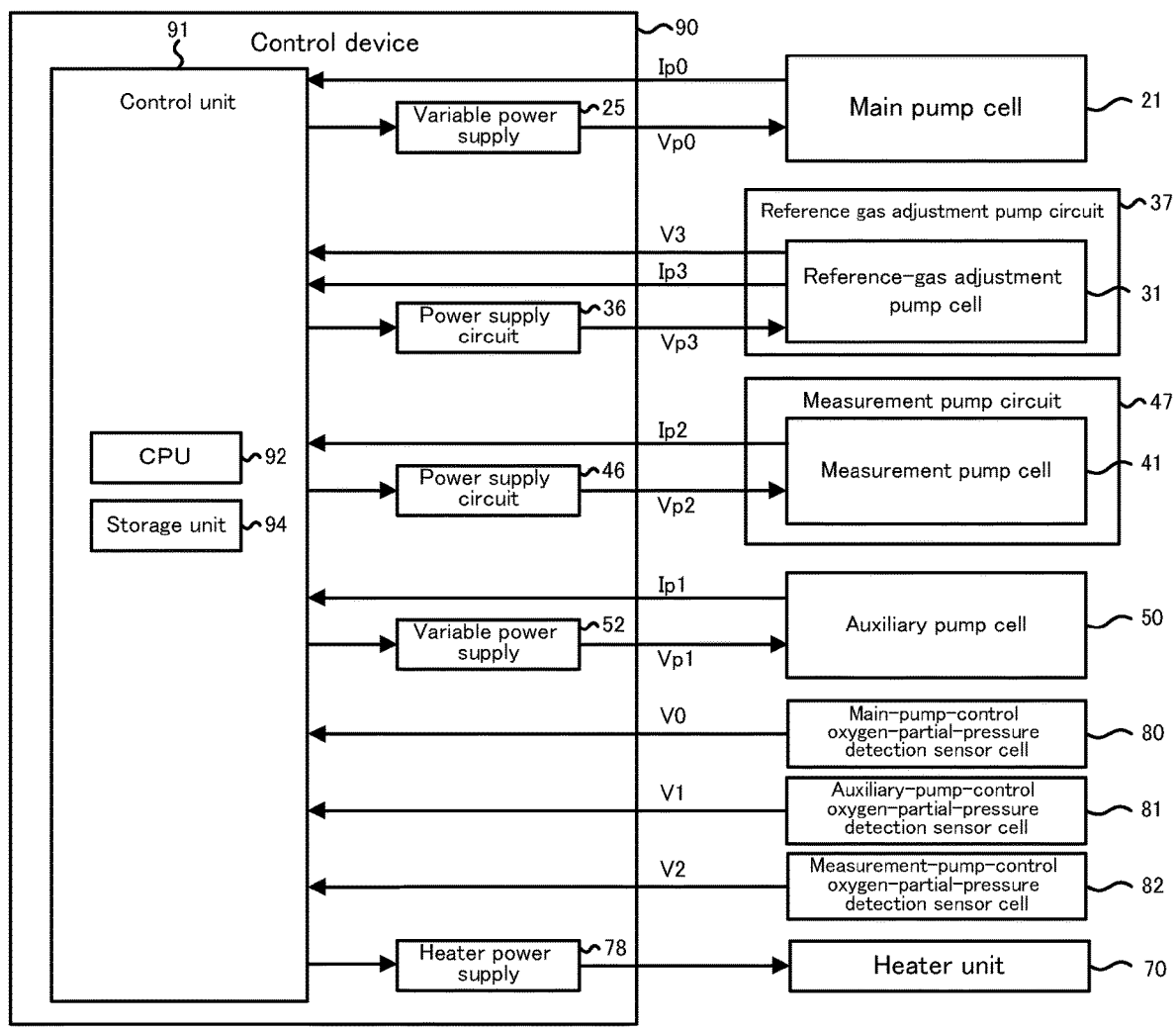
FIG. 3 is a block diagram illustrating an electrical connection relationship between a control device 90 and each cell.
Figure 4:
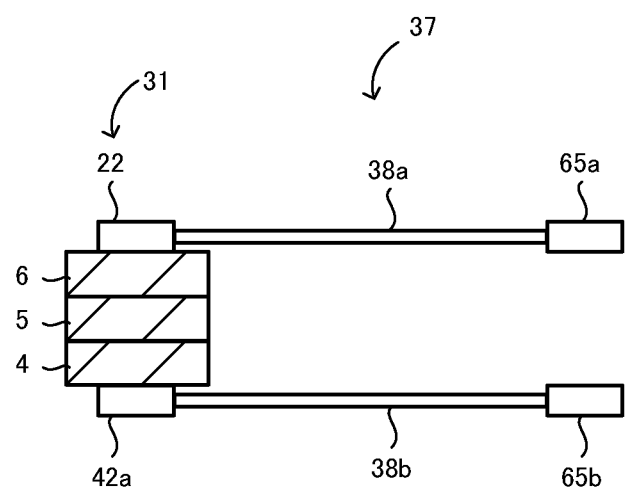
FIG. 4 is a schematic diagram schematically illustrating the configuration of a reference gas adjustment pump circuit 37.
Figure 5:
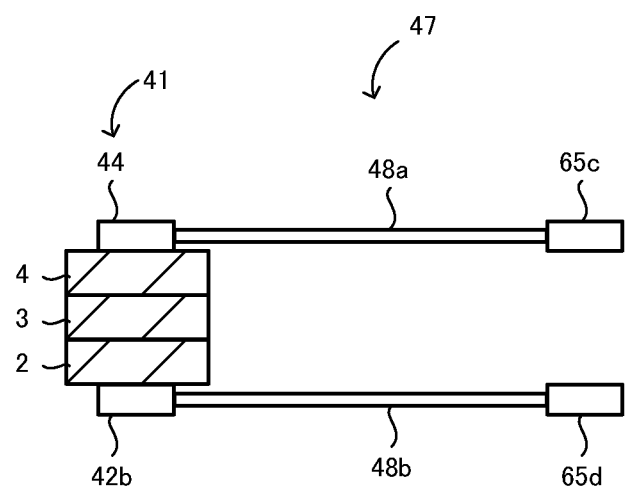
FIG. 5 is a schematic diagram schematically illustrating the configuration of a measurement pump circuit 47.

An embodiment of the present invention will now be described with reference to the drawings. FIG. 1 is a longitudinal sectional view of a gas sensor 100 according to an embodiment of the present invention. FIG. 2 is a schematic sectional view schematically illustrating an example configuration of a sensor element 101 included in the gas sensor 100. FIG. 3 is a block diagram illustrating an electrical connection relationship between a control device 90 and each cell. FIG. 4 is a schematic diagram schematically illustrating the configuration of a reference gas adjustment pump circuit 37. FIG. 5 is a schematic diagram schematically illustrating the configuration of a measurement pump circuit 47. The sensor element 101 has a long, rectangular parallelepiped shape. The longitudinal direction of the sensor element 101 (the left-right direction in FIG. 2) is represented as a front-rear direction, and the thickness direction of the sensor element 101 (the up-down direction in FIG. 2) is represented as an up-down direction. The width direction of the sensor element 101 (a direction perpendicular to the front-rear direction and the up-down direction) is represented as a left-right direction.

As illustrated in FIG. 1, the gas sensor 100 includes the sensor element 101, a protective cover 130 that protects the front end side of the sensor element 101, and a sensor assembly 140. The sensor assembly 140 includes a connector 150 to be brought into electrical conduction with the sensor element 101. As illustrated in FIG. 1, the gas sensor 100 is attached to, for example, a pipe 190 such as an exhaust gas pipe of a vehicle and is used to measure the concentration of a specific gas such as NOx or $O_2$ contained in an exhaust gas serving as a measurement-object gas. In this embodiment, the gas sensor 100 is configured to measure a NOx concentration as a specific gas concentration.

The protective cover 130 includes a bottomed cylindrical inner protective cover 131 that covers a front end of the sensor element 101, and a bottomed cylindrical outer protective cover 132 that covers the inner protective cover 131. The inner protective cover 131 and the outer protective cover 132 have formed therein a plurality of holes through which the measurement-object gas flows into the protective cover 130. A sensor element chamber 133 is formed as a space surrounded by the inner protective cover 131, and the front end of the sensor element 101 is arranged in the sensor element chamber 133.

The sensor assembly 140 includes an element sealing body 141 that seals the sensor element 101 in a fixed manner, a bolt 147 attached to the element sealing body 141, an outer cylinder 148, and the connector 150. The connector 150 is in contact with connector electrodes (only a connector electrode 65a and a heater connector electrode 71, which will be described below, are illustrated in FIGS. 1 and 2) formed on surfaces (upper and lower surfaces) of a rear end of the sensor element 101 and is electrically connected to the connector electrodes.

The element sealing body 141 includes a cylindrical main metal fitting 142, a cylindrical inner cylinder 143 coaxially welded to the main metal fitting 142 in a fixed manner, and ceramic supporters 144a to 144c, green compacts 145a and 145b, and a metal ring 146, which are sealed in a through hole inside the main metal fitting 142 and the inner cylinder 143. The sensor element 101 is located along the center axis of the element sealing body 141 in such a manner as to extend through the element sealing body 141 in the front-rear direction. The inner cylinder 143 has a reduced diameter portion 143a for pressing the green compact 145b in a direction toward the center axis of the inner cylinder 143, and a reduced diameter portion 143b for pressing the ceramic supporters 144a to 144c and the green compacts 145a and 145b to the front via the metal ring 146. The pressing forces from the reduced diameter portions 143a and 143b compress the green compacts 145a and 145b between the sensor element 101 and the set of the main metal fitting 142 and the inner cylinder 143. Accordingly, the green compacts 145a and 145b perform sealing between the sensor element chamber 133 in the protective cover 130 and a space 149 in the outer cylinder 148, and fix the sensor element 101.

The bolt 147 is coaxially fixed to the main metal fitting 142, and has a male threaded portion formed on an outer peripheral surface thereof. The male threaded portion of the bolt 147 is inserted into a fixing member 191 having a female threaded portion on an inner peripheral surface thereof. The fixing member 191 is welded to the pipe 190. Accordingly, the gas sensor 100 is fixed to the pipe 190 in such a manner that a portion of the gas sensor 100 corresponding to the front end of the sensor element 101 and the protective cover 130 projects into the pipe 190.

The outer cylinder 148 surrounds the inner cylinder 143, the sensor element 101, and the connector 150. A plurality of lead wires 155 connected to the connector 150 are drawn out from a rear end of the outer cylinder 148. The lead wires 155 are in electrical conduction with electrodes (described below) of the sensor element 101 via the connector 150. A gap between the outer cylinder 148 and the lead wires 155 is sealed with a rubber stopper 157. The space 149 in the outer cylinder 148 is filled with a reference gas (in this embodiment, air). The rear end of the sensor element 101 is arranged in the space 149.

The sensor element 101 is an element including a layered body having six layers, each of which is formed of an oxygen-ion-conductive solid electrolyte layer such as a zirconia ($ZrO_2$) layer. The six layers include a first substrate layer 1, a second substrate layer 2, a third substrate layer 3, a first solid electrolyte layer 4, a spacer layer 5, and a second solid electrolyte layer 6 and are stacked in the stated order from bottom to top in FIG. 2. The solid electrolyte forming the six layers is dense and gas-tight. The sensor element 101 is manufactured by, for example, after performing predetermined processing and circuit pattern printing on ceramic green sheets, each corresponding to one of the layers, stacking the ceramic green sheets, firing the stacked ceramic green sheets, and combining the fired ceramic green sheets together to form a single unit.

At one end of the sensor element 101 (in the left-hand portion of FIG. 2), a gas inlet 10, a first diffusion control section 11, a buffer space 12, a second diffusion control section 13, a first internal cavity 20, a third diffusion control section 30, a second internal cavity 40, a fourth diffusion control section 60, and a third internal cavity 61 are formed adjacent and communicate in the stated order between a lower surface of the second solid electrolyte layer 6 and an upper surface of the first solid electrolyte layer 4.

The gas inlet 10, the buffer space 12, the first internal cavity 20, the second internal cavity 40, and the third internal cavity 61 are internal spaces of the sensor element 101, which are formed by removing a portion of the spacer layer 5, with the tops thereof defined by the lower surface of the second solid electrolyte layer 6, the bottoms thereof defined by the upper surface of the first solid electrolyte layer 4, and the sides thereof defined by the side surfaces of the spacer layer 5.

The first diffusion control section 11, the second diffusion control section 13, and the third diffusion control section 30 are each provided as two horizontally long slits (whose openings have a longitudinal direction along a direction perpendicular to the drawing). The fourth diffusion control section 60 is disposed as a single horizontally long slit (whose opening has a longitudinal direction along a direction perpendicular to the drawing), which is formed as a gap from the lower surface of the second solid electrolyte layer 6. Note that the portion from the gas inlet 10 up to the third internal cavity 61 is also referred to as a measurement-object gas flow section.

A reference gas chamber 49 is disposed between a lower surface of the first solid electrolyte layer 4 and an upper surface of the second substrate layer 2. The reference gas chamber 49 is an internal space of the sensor element 101, which is formed by removing a portion of the third substrate layer 3. The reference gas chamber 49 is formed as an independent space that is not open to outside the sensor element 101, unlike the measurement-object gas flow section. The reference gas chamber 49 is arranged underneath the first internal cavity 20. The reference gas chamber 49 is configured to store a reference gas serving as a reference to measure the NOx concentration. The reference gas is a gas having a predetermined oxygen concentration and is atmospheric air in this embodiment. The reference gas chamber 49 is provided with a first reference electrode 42a and a second reference electrode 42b.

The first reference electrode 42a is a porous electrode disposed on the lower surface of the first solid electrolyte layer 4. The second reference electrode 42b is a porous electrode disposed on the upper surface of the second substrate layer 2. As described below, the second reference electrode 42b can be used to measure the oxygen concentration (oxygen partial pressure) in the first internal cavity 20, the second internal cavity 40, and the third internal cavity 61. The first reference electrode 42a and the second reference electrode 42b are each formed as a porous cermet electrode (e.g., a cermet electrode composed of Pt and $ZrO_2$).

In the measurement-object gas flow section, the gas inlet 10 is a portion open to an external space such that the measurement-object gas is taken into the sensor element 101 from the external space through the gas inlet 10. The first diffusion control section 11 is a portion that applies a predetermined diffusion resistance to the measurement-object gas taken through the gas inlet 10. The buffer space 12 is a space provided to guide the measurement-object gas introduced through the first diffusion control section 11 to the second diffusion control section 13. The second diffusion control section 13 is a portion that applies a predetermined diffusion resistance to the measurement-object gas to be introduced into the first internal cavity 20 from the buffer space 12. When the measurement-object gas is introduced into the first internal cavity 20 from outside the sensor element 101, the measurement-object gas, which is rapidly taken into the sensor element 101 through the gas inlet 10 due to changes in the pressure of the measurement-object gas in the external space (pulsations in exhaust pressure in a case where the measurement-object gas is an exhaust gas of an automobile), is not directly introduced into the first internal cavity 20, but is introduced into the first internal cavity 20 after the changes in the pressure of the measurement-object gas are compensated for through the first diffusion control section 11, the buffer space 12, and the second diffusion control section 13. Consequently, the changes in the pressure of the measurement-object gas to be introduced into the first internal cavity 20 are almost negligible. The first internal cavity 20 is provided as a space for adjusting the oxygen partial pressure in the measurement-object gas introduced through the second diffusion control section 13. The oxygen partial pressure is adjusted by the operation of a main pump cell 21.

The main pump cell 21 is an electrochemical pump cell including an inner pump electrode 22 having a ceiling electrode portion 22a disposed over substantially the entire lower surface of a portion of the second solid electrolyte layer 6 facing the first internal cavity 20, an outer pump electrode 23 disposed in a region on an upper surface of the second solid electrolyte layer 6 corresponding to the ceiling electrode portion 22a in such a manner that the outer pump electrode 23 is exposed to the external space (the sensor element chamber 133 in FIG. 1), and the second solid electrolyte layer 6 held between the electrodes 22 and 23.

The inner pump electrode 22 is formed across the upper and lower solid electrolyte layers defining the first internal cavity 20 (i.e., the second solid electrolyte layer 6 and the first solid electrolyte layer 4), and the spacer layer 5 forming the sidewalls. Specifically, the ceiling electrode portion 22a is formed on the lower surface of the second solid electrolyte layer 6, which forms a ceiling surface of the first internal cavity 20. A bottom electrode portion 22b is formed directly on the upper surface of the first solid electrolyte layer 4, which forms a bottom surface of the first internal cavity 20. Side electrode portions (not illustrated) are formed on sidewall surfaces (inner surfaces) of the spacer layer 5, which form both sidewall portions of the first internal cavity 20, so as to connect the ceiling electrode portion 22a and the bottom electrode portion 22b to each other. The inner pump electrode 22 is thus disposed to have a tunnel structure in the portion where the side electrode portions are disposed.

The inner pump electrode 22 and the outer pump electrode 23 are each formed as a porous cermet electrode (e.g., a cermet electrode composed of Pt and $ZrO_2$ containing 1% Au). The inner pump electrode 22, which comes into contact with the measurement-object gas, is formed of a material having lowered reduction ability for the NOx component in the measurement-object gas.

In the main pump cell 21, a desired pump voltage Vp0 is applied between the inner pump electrode 22 and the outer pump electrode 23 to cause a pump current Ip0 to flow between the inner pump electrode 22 and the outer pump electrode 23 in the positive direction or the negative direction. Accordingly, the main pump cell 21 is capable of pumping out oxygen to the external space from the first internal cavity 20 or pumping oxygen into the first internal cavity 20 from the external space.

Further, the inner pump electrode 22, the second solid electrolyte layer 6, the spacer layer 5, the first solid electrolyte layer 4, the third substrate layer 3, the second substrate layer 2, and the second reference electrode 42b form an electrochemical sensor cell, namely, a main-pump-control oxygen-partial-pressure detection sensor cell 80, for detecting the oxygen concentration (oxygen partial pressure) in the atmosphere in the first internal cavity 20.

An electromotive force (voltage V0) in the main-pump-control oxygen-partial-pressure detection sensor cell 80 is measured to determine the oxygen concentration (oxygen partial pressure) in the first internal cavity 20. In addition, feedback control is performed on the pump voltage Vp0 of a variable power supply 25 so that the electromotive force V0 becomes a target value to control the pump current Ip0. Accordingly, the oxygen concentration in the first internal cavity 20 can be kept at a predetermined constant value.

The third diffusion control section 30 is a portion that applies a predetermined diffusion resistance to the measurement-object gas in which the oxygen concentration (oxygen partial pressure) is controlled in the first internal cavity 20 by the operation of the main pump cell 21 to guide the measurement-object gas into the second internal cavity 40.

The second internal cavity 40 is provided as a space for, after the adjustment of the oxygen concentration (oxygen partial pressure) in the first internal cavity 20 in advance, further adjusting the oxygen partial pressure in the measurement-object gas introduced through the third diffusion control section 30 by using an auxiliary pump cell 50. Accordingly, the oxygen concentration in the second internal cavity 40 can be kept constant with high accuracy, and thus the gas sensor 100 can accurately measure the NOx concentration.

The auxiliary pump cell 50 is an auxiliary electrochemical pump cell including an auxiliary pump electrode 51 having a ceiling electrode portion 51a disposed over substantially the entire lower surface of a portion of the second solid electrolyte layer 6 facing the second internal cavity 40, the outer pump electrode 23 (or any other suitable electrode on the outer side of the sensor element 101 in place of the outer pump electrode 23), and the second solid electrolyte layer 6.

The auxiliary pump electrode 51 has a tunnel structure similar to that of the inner pump electrode 22 disposed in the first internal cavity 20 described above, and is disposed in the second internal cavity 40. That is, the ceiling electrode portion 51a is formed on the lower surface of the second solid electrolyte layer 6, which forms a ceiling surface of the second internal cavity 40. A bottom electrode portion 51b is formed directly on the upper surface of the first solid electrolyte layer 4, which forms a bottom surface of the second internal cavity 40. Side electrode portions (not illustrated) connecting the ceiling electrode portion 51a and the bottom electrode portion 51b to each other are formed on both sidewall surfaces of the spacer layer 5, which form sidewalls of the second internal cavity 40. Thus, the tunnel structure is provided. Like the inner pump electrode 22, the auxiliary pump electrode 51 is also formed of a material having lowered reduction ability for the NOx component in the measurement-object gas.

In the auxiliary pump cell 50, a desired voltage Vp1 is applied between the auxiliary pump electrode 51 and the outer pump electrode 23. Accordingly, the auxiliary pump cell 50 is capable of pumping out oxygen in the atmosphere in the second internal cavity 40 to the external space or pumping oxygen into the second internal cavity 40 from the external space.

Further, the auxiliary pump electrode 51, the second reference electrode 42b, the second solid electrolyte layer 6, the spacer layer 5, the first solid electrolyte layer 4, the third substrate layer 3, and the second substrate layer 2 form an electrochemical sensor cell, namely, an auxiliary-pump-control oxygen-partial-pressure detection sensor cell 81, for controlling the oxygen partial pressure in the atmosphere in the second internal cavity 40.

The auxiliary pump cell 50 performs pumping using a variable power supply 52 whose voltage is controlled on the basis of an electromotive force (voltage V1) detected by the auxiliary-pump-control oxygen-partial-pressure detection sensor cell 81. Accordingly, the oxygen partial pressure in the atmosphere in the second internal cavity 40 is controlled to a low partial pressure that does not substantially affect NOx measurement.

Additionally, a pump current Ip1 is used to control the electromotive force of the main-pump-control oxygen-partial-pressure detection sensor cell 80. Specifically, the pump current Ip1 is input as a control signal to the main-pump-control oxygen-partial-pressure detection sensor cell 80, for which the target value of the voltage V0 described above is controlled to perform control so that the gradient of the oxygen partial pressure in the measurement-object gas to be introduced into the second internal cavity 40 from the third diffusion control section 30 remains always constant. When the gas sensor 100 is used as a NOx sensor, the oxygen concentration in the second internal cavity 40 is kept at a constant value of about 0.001 ppm by the operation of the main pump cell 21 and the auxiliary pump cell 50.

The fourth diffusion control section 60 is a portion that applies a predetermined diffusion resistance to the measurement-object gas in which the oxygen concentration (oxygen partial pressure) is controlled in the second internal cavity 40 by the operation of the auxiliary pump cell 50 to guide the measurement-object gas into the third internal cavity 61. The fourth diffusion control section 60 serves to limit the amount of NOx flowing into the third internal cavity 61.

The third internal cavity 61 is provided as a space for, after the adjustment of the oxygen concentration (oxygen partial pressure) in the second internal cavity 40 in advance, performing a process on the measurement-object gas introduced through the fourth diffusion control section 60 to measure the nitrogen oxide (NOx) concentration in the measurement-object gas. The measurement of the NOx concentration is mainly performed in the third internal cavity 61 by the operation of a measurement pump cell 41.

The measurement pump cell 41 measures the NOx concentration in the measurement-object gas in the third internal cavity 61. The measurement pump cell 41 is an electrochemical pump cell including a measurement electrode 44 disposed directly on a portion of the upper surface of the first solid electrolyte layer 4 facing the third internal cavity 61, the second reference electrode 42b, the first solid electrolyte layer 4, the third substrate layer 3, and the second substrate layer 2. The measurement electrode 44 is a porous cermet electrode (e.g., a cermet electrode composed of Pt and $ZrO_2$) composed of a material having higher reduction ability for the NOx component in the measurement-object gas than the material of the inner pump electrode 22. The measurement electrode 44 also functions as a NOx reducing catalyst for reducing NOx present in the atmosphere in the third internal cavity 61.

The measurement pump cell 41 is capable of pumping oxygen produced by decomposition of nitrogen oxide in the atmosphere around the measurement electrode 44 into around the second reference electrode 42b, that is, into the reference gas chamber 49, and detecting the amount of produced oxygen as a pump current Ip2.

Further, the measurement electrode 44, the second reference electrode 42b, the first solid electrolyte layer 4, the third substrate layer 3, and the second substrate layer 2 form an electrochemical sensor cell, namely, a measurement-pump-control oxygen-partial-pressure detection sensor cell 82, for detecting the oxygen partial pressure around the measurement electrode 44. A power supply circuit 46 is controlled on the basis of an electromotive force (voltage V2) detected by the measurement-pump-control oxygen-partial-pressure detection sensor cell 82.

The measurement-object gas guided into the second internal cavity 40, in which the oxygen partial pressure is controlled, passes through the fourth diffusion control section 60 and reaches the measurement electrode 44 in the third internal cavity 61. In the measurement-object gas around the measurement electrode 44, nitrogen oxide is reduced to produce oxygen ($2NO \rightarrow N_2+O_2$). The produced oxygen is pumped by the measurement pump cell 41. In the pumping process, a voltage Vp2 of the power supply circuit 46 is controlled so that the voltage V2 detected by the measurement-pump-control oxygen-partial-pressure detection sensor cell 82 becomes constant (a target value). Since the amount of oxygen produced around the measurement electrode 44 is proportional to the nitrogen oxide concentration in the measurement-object gas, the nitrogen oxide concentration in the measurement-object gas is calculated using the pump current Ip2 in the measurement pump cell 41.

Further, the second solid electrolyte layer 6, the spacer layer 5, the first solid electrolyte layer 4, the inner pump electrode 22, and the first reference electrode 42a form an electrochemical reference-gas adjustment pump cell 31. The reference-gas adjustment pump cell 31 performs pumping in response to the flow of a pump current Ip3 by the application of a control voltage Vp3 from a power supply circuit 36 connected between the inner pump electrode 22 and the first reference electrode 42a. Accordingly, the reference-gas adjustment pump cell 31 pumps oxygen into the space around the first reference electrode 42a, that is, the reference gas chamber 49, from the space around the inner pump electrode 22, that is, the first internal cavity 20. A voltage V3 of the reference-gas adjustment pump cell 31 can be measured.

In the gas sensor 100 having the configuration described above, the main pump cell 21 and the auxiliary pump cell 50 are activated to provide the measurement pump cell 41 with the measurement-object gas in which the oxygen partial pressure is always kept at a constant low value (a value that does not substantially affect NOx measurement). Accordingly, the NOx concentration in the measurement-object gas can be determined on the basis of the pump current Ip2 caused to flow by the measurement pump cell 41 pumping out oxygen produced by reducing NOx, approximately in proportion to the concentration of NOx in the measurement-object gas.

The sensor element 101 further includes a heater unit 70 that serves to perform temperature adjustment to heat the sensor element 101 and keep the temperature steady to enhance the oxygen ion conductivity of the solid electrolyte. The heater unit 70 includes a heater connector electrode 71, a heater 72, a through hole 73, a heater insulating layer 74, and a lead wire 76.

The heater connector electrode 71 is an electrode formed in contact with a lower surface of the first substrate layer 1. Power can be fed to the heater unit 70 from the outside by connecting the heater connector electrode 71 to a heater power supply 78.

The heater 72 is an electric resistor formed to be vertically held between the first substrate layer 1 and the second substrate layer 2. The heater 72 is connected to the heater connector electrode 71 via the lead wire 76 and the through hole 73. The heater 72 generates heat in response to power being fed thereto from the outside through the heater connector electrode 71 to heat the solid electrolyte forming the sensor element 101 and keep the temperature steady.

The heater 72 is embedded across an entire area from the first internal cavity 20 to the third internal cavity 61 and is capable of adjusting the temperature of the entire sensor element 101 to a temperature at which the solid electrolyte is activated.

The heater insulating layer 74 is an insulating layer composed of porous alumina, which is formed of an insulating material such as alumina on upper and lower surfaces of the heater 72. The heater insulating layer 74 is formed to provide electrical insulation between the first substrate layer 1 and the heater 72 and electrical insulation between the second substrate layer 2 and the heater 72.

As illustrated in FIG. 3, the control device 90 includes the variable power supplies 25 and 52 described above, the power supply circuits 36 and 46 described above, the heater power supply 78 described above, and a control unit 91. The control unit 91 is a known microprocessor including a CPU 92 and a storage unit 94. The storage unit 94 includes, for example, a RAM, a ROM, and so on. The control unit 91 receives the voltage V0 detected by the main-pump-control oxygen-partial-pressure detection sensor cell 80, the voltage V1 detected by the auxiliary-pump-control oxygen-partial-pressure detection sensor cell 81, the voltage V2 detected by the measurement-pump-control oxygen-partial-pressure detection sensor cell 82, the voltage V3 detected by the reference-gas adjustment pump cell 31, the pump current Ip0 detected by the main pump cell 21, the pump current Ip1 detected by the auxiliary pump cell 50, the pump current Ip2 detected by the measurement pump cell 41, and the pump current Ip3 detected by the reference-gas adjustment pump cell 31. The control unit 91 outputs control signals to the variable power supplies 25 and 52 to control the voltages Vp0 and Vp1, thereby controlling the main pump cell 21 and the auxiliary pump cell 50. The control unit 91 outputs control signals to the power supply circuits 36 and 46 to control the voltages Vp3 and Vp2, thereby controlling the reference-gas adjustment pump cell 31 and the measurement pump cell 41. The control unit 91 outputs a control signal to the heater power supply 78 to control the power to be supplied to the heater 72, thereby controlling the heater 72.

The control unit 91 performs feedback control of the pump voltage Vp0 of the variable power supply 25 so that the voltage V0 becomes a target value V0* (i.e., the oxygen concentration in the first internal cavity 20 becomes a target concentration).

The control unit 91 performs feedback control of the voltage Vp1 of the variable power supply 52 so that the voltage V1 becomes a target value V1* (i.e., the oxygen concentration in the second internal cavity 40 becomes a predetermined low oxygen concentration that does not substantially affect NOx measurement). Additionally, the control unit 91 sets (performs feedback control of) the target value V0* of the voltage V0 on the basis of the pump current Ip1 so that the pump current Ip1 flowing by the application of the voltage Vp1 becomes a target value Ip1*. Accordingly, the gradient of the oxygen partial pressure in the measurement-object gas to be introduced into the second internal cavity 40 from the third diffusion control section 30 remains always constant.

The control unit 91 performs feedback control of the voltage Vp2 of the power supply circuit 46 so that the voltage V2 becomes a target value V2* (i.e., the concentration of oxygen produced by reducing the nitrogen oxide in the measurement-object gas in the third internal cavity 61 becomes substantially zero), and calculates the NOx concentration in the measurement-object gas on the basis of the pump current Ip2. The target value V2* is determined in advance as a value at which the pump current Ip2 flowing by the application of the voltage Vp2 subjected to feedback control becomes a limiting current. As can be seen from FIG. 2, both the voltage Vp2 and the voltage V2 are basically voltages between the measurement electrode 44 and the second reference electrode 42b. During the application the voltage Vp2, the voltage V2 is affected by the voltage Vp2. Accordingly, preferably, the voltage Vp2 output from the power supply circuit 46 is set to, for example, a voltage that is repeatedly turned on and off, such as a pulsed voltage, and the control unit 91 measures the value of the voltage V2 during a period in which the voltage Vp2 is off, and performs feedback control so that the voltage V2 becomes the target value V2*. When the pump current Ip2 flows, as described above, oxygen in the third internal cavity 61 is pumped into the reference gas chamber 49.

The control unit 91 controls the power supply circuit 36 so that the constant voltage Vp3 (e.g., a DC voltage) is applied to the reference-gas adjustment pump cell 31, and causes the pump current Ip3 to flow. Accordingly, oxygen is pumped into the reference gas chamber 49 from the first internal cavity 20.

Further, the control unit 91 measures the voltage V3 of the reference-gas adjustment pump cell 31, and measures the resistance value of the reference-gas adjustment pump cell 31 on the basis of the voltage V3 and the pump current Ip3. The control unit 91 controls the heater power supply 78 on the basis of the measured resistance value to control the power to be supplied to the heater 72. For example, the control unit 91 calculates the temperature of the first solid electrolyte layer 4, which is a portion of the reference-gas adjustment pump cell 31, on the basis of the measured resistance value, and controls the heater power supply 78 so that the temperature becomes a target value. Accordingly, the control unit 91 adjusts the temperature of the cells 21, 31, 41, 50, 80, 81, and 82 of the sensor element 101 (in particular, the temperature of the solid electrolyte layers forming portions of these cells) to a predetermined driving temperature at which the solid electrolyte is activated. The driving temperature may be, for example, greater than or equal to 700° C. and less than or equal to 900° C.

The control unit 91 may measure the resistance value of the reference-gas adjustment pump cell 31 while no oxygen is pumped into the reference gas chamber 49 by the reference-gas adjustment pump cell 31. In this case, the control unit 91 may control the power supply circuit 36 to apply a relatively small voltage Vp3, and measure the resistance value of the reference-gas adjustment pump cell 31 on the basis of the weak values of the pump current Ip3 and the voltage V3 obtained at this time.

Although schematically illustrated in FIGS. 2 and 3, the electrodes of the sensor element 101 and the control device 90 are actually connected to each other via leads and connector electrodes disposed in the sensor element 101 and the connector 150 and the lead wires 155 illustrated in FIG. 1. The following describes this point in detail.

The sensor element 101 includes the reference gas adjustment pump circuit 37 illustrated in FIG. 4 and the measurement pump circuit 47 illustrated in FIG. 5. The reference gas adjustment pump circuit 37 includes the reference-gas adjustment pump cell 31, leads 38a and 38b, and connector electrodes 65a and 65b. The measurement pump circuit 47 includes the measurement pump cell 41, leads 48a and 48b, and connector electrodes 65c and 65d.

The connector electrodes 65a to 65d are disposed on the outer side of the sensor element 101. In this embodiment, the connector electrodes 65a to 65d are disposed on the upper surface of the sensor element 101, that is, at the rear end of the upper surface of the second solid electrolyte layer 6 (only the connector electrode 65a is illustrated in FIG. 2). However, for example, one or more of the connector electrodes 65a to 65d may be disposed on the lower surface of the sensor element 101, that is, at the rear end of the lower surface of the first substrate layer 1.

The lead 38a is a conductor that connects the inner pump electrode 22 of the reference-gas adjustment pump cell 31 to the connector electrode 65a. The lead 38b is a conductor that connects the first reference electrode 42a of the reference-gas adjustment pump cell 31 to the connector electrode 65b. The lead 48a is a conductor that connects the measurement electrode 44 of the measurement pump cell 41 to the connector electrode 65c. The lead 48b is a conductor that connects the second reference electrode 42b of the measurement pump cell 41 to the connector electrode 65d. The lead 38a includes a strip-shaped conductor formed on the upper surface of the first solid electrolyte layer 4 and disposed between the first solid electrolyte layer 4 and the spacer layer 5. The lead 38b includes a strip-shaped conductor formed on the lower surface of the first solid electrolyte layer 4 and disposed between the first solid electrolyte layer 4 and the third substrate layer 3. The lead 48a includes a strip-shaped conductor formed on the upper surface of the first solid electrolyte layer 4 and disposed between the first solid electrolyte layer 4 and the spacer layer 5. The lead 48b includes a strip-shaped conductor formed on the upper surface of the second substrate layer 2 and disposed between the third substrate layer 3 and the second substrate layer 2.

The lead 38a is routed inside or outside the sensor element 101 so that the inner pump electrode 22 disposed on the lower side of the second solid electrolyte layer 6 and the connector electrode 65a disposed on the upper side of the second solid electrolyte layer 6 can be connected to each other. For example, the lead 38a may include, in addition to the conductor between the first solid electrolyte layer 4 and the spacer layer 5, at least one of a strip-shaped conductor disposed on the outer side of the sensor element 101 and a conductor in a through hole extending through the second solid electrolyte layer 6. Each of the leads 38b, 48a, and 48b may also be routed inside or outside the sensor element 101 and include at least one of a strip-shaped conductor disposed on the outer side of the sensor element 101 and a conductor in a through hole extending through the corresponding solid electrolyte layer of the sensor element 101. The leads 38a, 38b, 48a, and 48b are covered with respective insulating layers (not illustrated) such that electrical insulation from the surrounding solid electrolyte layers is maintained.

The control device 90 and the reference-gas adjustment pump cell 31 are connected to each other via the connector electrodes 65a and 65b and the leads 38a and 38b of the reference gas adjustment pump circuit 37. The control device 90 and the measurement pump cell 41 are connected to each other via the connector electrodes 65c and 65d and the leads 48a and 48b of the measurement pump circuit 47. The same applies to the other cells 21, 50, 80, 81, and 82, although connector electrodes and leads are not illustrated. Each of the plurality of electrodes of the sensor element 101 is in electrical conduction with one connector electrode. Accordingly, for example, the control device 90 and the second reference electrode 42b, which is a portion of the main-pump-control oxygen-partial-pressure detection sensor cell 80, are also connected to each other via the lead 48b and the connector electrode 65d.

Each of the leads 38a, 38b, 48a, and 48b contains a noble metal as a main component. The term "main component" refers to a component with a volume proportion greater than or equal to 50 volume % or a component with the highest volume proportion among all the components. Each of the leads 38a, 38b, 48a, and 48b may contain a noble metal and inevitable impurities. In this embodiment, the noble metals contained in the leads 38a, 38b, 48a, and 48b are Pt. The lead 38b may have dimensions, for example, greater than or equal to 0.35 mm and less than or equal to 0.45 mm in width and greater than or equal to 10 μm and less than or equal to 30 μm in thickness. The lead 48b may have dimensions, for example, greater than or equal to 0.35 mm and less than or equal to 0.45 mm in width and greater than or equal to 10 μm and less than or equal to 30 μm in thickness. At least one of the lead 38a and the lead 48a may also have a width greater than or equal to 0.35 mm and less than or equal to 0.45 mm and a thickness greater than or equal to 10 μm and less than or equal to 30 μm.

Each of the connector electrodes 65a to 65d contains a noble metal as a main component. Each of the connector electrodes 65a to 65d may contain a noble metal and inevitable impurities. In this embodiment, the noble metals contained the connector electrodes 65a to 65d are Pt.

A porosity P2 of the lead 48b is higher than a porosity P1 of the lead 38b. That is, at least the lead 48b among the leads 38b and 48b is porous. In the sensor element 101, therefore, the porous lead 48b is connected to the second porous reference electrode 42b. Thus, oxygen pumped into the reference gas chamber 49 by the reference-gas adjustment pump cell 31 and the measurement pump cell 41 can be released to outside the sensor element 101 (e.g., the space 149 in the outer cylinder 148) through the pores in the second reference electrode 42b and the pores in the lead 48b. This makes it possible to suppress an increase in oxygen concentration in the reference gas chamber 49. Accordingly, the inside of the reference gas chamber 49 is easily maintained at a predetermined oxygen concentration (here, the same oxygen concentration as that of atmospheric air). A change in oxygen concentration in the reference gas chamber 49 causes, for example, a change in voltage based on the first reference electrode 42a or the second reference electrode 42b, such as the voltage V2, which may affect the control of the sensor element 101 by the control device 90. As a result, the detection accuracy of the NOx concentration may deteriorate. Maintaining the inside of the reference gas chamber 49 at a predetermined oxygen concentration can suppress the deterioration of the detection accuracy of the NOx concentration.

The porosities P1 and P2 are assumed to be values derived in the following way by using an image (SEM image) obtained through observation with a scanning electron microscope (SEM). First, the measurement target is cut so that the cross section of the measurement target is an observation surface, and the cut section is subjected to resin embedding and polishing to obtain a specimen for observation. Subsequently, a SEM photograph (secondary electron image at an acceleration voltage of 15 kV and a magnification of 1000) of the observation surface of the specimen for observation is taken to obtain an SEM image of the measurement target. Then, the obtained image is subjected to image analysis to determine a threshold value from the luminance distribution of luminance data of pixels in the image by using a discriminant analysis method (Otsu's binarization). Thereafter, each pixel in the image is binarized into a substance portion and a pore portion on the basis of the determined threshold value, and the area of the substance portion and the area of the pore portion are calculated. Then, the proportion of the area of the pore portion in the total area (the sum of the area of the substance portion and the area of the pore portion) is derived as a porosity (expressed in %).

A portion of the surface of the lead 48b may be exposed to the reference gas chamber 49 without being covered with the insulating layer so that oxygen in the reference gas chamber 49 can directly pass through the pores of the lead 48b. In this embodiment, furthermore, the connector electrode 65d is also formed to be porous to ensure that oxygen in the lead 48b can be discharged to the space 149. Instead of making the connector electrode 65d porous, the surface (e.g., the upper surface) of the lead 48b disposed on the outer surface (e.g., the upper surface) of the sensor element 101 may be exposed to the outside (here, the space 149) without being covered with the insulating layer.

The lead 38b may also be porous. In this case, oxygen in the reference gas chamber 49 may also be released to outside the sensor element 101 through the pores in the first porous reference electrode 42a and the pores in the lead 38b.

Further, a resistance value R2 between the connector electrode 65c and the connector electrode 65d of the measurement pump circuit 47 is higher than a resistance value P1 between the connector electrode 65a and the connector electrode 65b of the reference gas adjustment pump circuit 37. That is, in this embodiment, resistance value R2>resistance value P1 and porosity P2>porosity P1 are satisfied. Accordingly, the lead 48b of the measurement pump circuit 47 having a higher resistance value among the reference gas adjustment pump circuit 37 and the measurement pump circuit 47, which are two pump circuits for pumping oxygen into the reference gas chamber 49, has a higher porosity than the lead 38b of the reference gas adjustment pump circuit 37 having a lower resistance value. The higher the porosity of a lead, the more likely it is that the resistance value of the lead varies due to a manufacturing error. In the sensor element 101 according to this embodiment, however, the porosity P2 of the lead 48b, which is a lead included in the circuit having a higher overall resistance value among the reference gas adjustment pump circuit 37 and the measurement pump circuit 47, is set to a high value. Thus, even if the resistance value of the lead 48b varies for each sensor element 101, the influence on the resistance value R2, that is, the variation in the resistance value R2, is relatively small. In contrast, if the porosity P1 of the lead 38b is set to be high, the resistance value of the lead 38b varies for each sensor element 101. As a result, the influence on the resistance value R1, that is, the variation in the resistance value R1, is relatively large. In the sensor element 101 according to this embodiment, accordingly, for example, as compared with the case where the porosity P1 is greater than or equal to the porosity P2, individual differences for the manufacturing of a plurality of sensor elements 101 are small, that is, manufacturing variations are small. An increase in variations in the resistance values of circuits causes variations in current flowing under the control of the control device 90. As a result, manufacturing variations also occur in the operation of the sensor elements 101, and variations in the detection accuracy of the NOx concentration are likely to increase. A reduction in manufacturing variations for the sensor elements 101 can reduce the manufacturing variations in the detection accuracy of the NOx concentration, and can reduce the number of sensor elements 101 having low detection accuracy. Accordingly, the yield of the sensor elements 101 can be improved.

The resistance values R1 and R2 are values in a state where the sensor element 101 is in use. That is, the resistance values R1 and R2 are values in a state where a driving temperature (any temperature greater than or equal to 700° C. and less than or equal to 900° C.) at which the solid electrolyte of the sensor element 101 (in particular, the layers 2 to 6 forming at least portions of the reference-gas adjustment pump cell 31 and the measurement pump cell 41) is activated is obtained by the heater 72. In addition, the resistance values R1 and R2 are values in a state where the reference-gas adjustment pump cell 31 and the measurement pump cell 41 do not pump in oxygen. Most of the resistance value R1 is a resistance value of the solid electrolyte layers (here, the layers 4 to 6) between the inner pump electrode 22 and the first reference electrode 42a of the reference-gas adjustment pump cell 31. Most of the resistance value R2 is a resistance value of the solid electrolyte layers (here, the layers 2 to 4) between the measurement electrode 44 and the second reference electrode 42b of the measurement pump cell 41. In this embodiment, as illustrated in FIG. 2, the reference gas chamber 49 is located directly underneath the inner pump electrode 22, and the reference gas chamber 49 is arranged at a position closer to the inner pump electrode 22 than to the measurement electrode 44. The first reference electrode 42a is located above the second reference electrode 42b. Accordingly, since the distance between the inner pump electrode 22 and the first reference electrode 42a is smaller than the distance between the measurement electrode 44 and the second reference electrode 42b, resistance value R1<resistance value R2 is satisfied. In addition, although not illustrated in FIGS. 4 and 5, as can be seen from FIG. 2, a path through which a current (oxygen ions) flows between the inner pump electrode 22 and the first reference electrode 42a also includes a path extending through only the layer 4 without the intervention of the layers 5 and 6. As described above, since the inner pump electrode 22 also includes the side electrode portions, the path through which a current (oxygen ions) flows between the inner pump electrode 22 and the first reference electrode 42a also includes a path extending through only the layers 4 and 5 without the intervention of the layer 6. In contrast, a path through which a current (oxygen ions) flows between the measurement electrode 44 and the second reference electrode 42b includes only a path extending through the layers 2 to 4. Accordingly, the resistance value R1 is smaller than the resistance value R2.

The porosity P2 of the lead 48b is preferably greater than or equal to 5%, more preferably greater than 5%, and still more preferably greater than or equal to 10%. When the porosity P2 is greater than or equal to 5%, the effect of suppressing an increase in oxygen concentration in the reference gas chamber 49 is more reliably obtained. When the porosity P2 is greater than 5%, the effect of suppressing an increase in oxygen concentration in the reference gas chamber 49 is further more reliably obtained. When the porosity P2 is greater than or equal to 10%, the increase in oxygen concentration in the reference gas chamber 49 can still further be suppressed. The porosity P2 is preferably less than or equal to 25%. When the porosity P2 is less than or equal to 25%, a break in the lead 48b at the time of manufacturing the sensor element 101 can be suppressed. Likewise, the porosity of the second reference electrode 42b is preferably greater than or equal to 5%, more preferably greater than 5%, and still more preferably greater than or equal to 10%. The porosity of the second reference electrode 42b is preferably less than or equal to 25%. The porosity of the connector electrode 65d is preferably greater than or equal to 5%, more preferably greater than 5%, and still more preferably greater than or equal to 10%. The porosity of the connector electrode 65d is preferably less than or equal to 25%. The porosity of the connector electrode 65d may have the same value as the porosity P2 of the lead 48b. The porosity P1 of the lead 38b may be greater than or equal to 1%. The porosity P1 of the lead 38b may be less than or equal to 5% or may be less than 5%. The porosity P1 may be 0%.

The functions of the reference-gas adjustment pump cell 31 will now be described in detail. As described above, in the sensor element 101, the measurement pump cell 41 pumps oxygen into the reference gas chamber 49. Accordingly, the sensor element 101 is configured to release oxygen to the space 149 through the lead 48b to prevent an excessive amount of oxygen from being stored in the reference gas chamber 49. When the amount of oxygen pumped into the reference gas chamber 49 by the measurement pump cell 41 is small, such as when the NOx concentration is small, the gas may flow to the reference gas chamber 49 from the space 149 through the lead 48b. There is no problem even if such a phenomenon occurs since the atmosphere in the space 149 is usually the same as the reference gas. However, for example, due to the large pressure on the measurement-object gas side or the like, the measurement-object gas in the sensor element chamber 133 may slightly enter the space 149 although the sensor element chamber 133 and the space 149 are separated by the sensor assembly 140 (in particular, the green compacts 145a and 145b). Accordingly, if the oxygen concentration in the reference gas chamber 49 is reduced, for example, a voltage based on the first reference electrode 42a or the second reference electrode 42b, such as the voltage V2, may be changed, and the detection accuracy of the NOx concentration may deteriorate. The reference-gas adjustment pump cell 31 pumps oxygen into the reference gas chamber 49, thereby suppressing the reduction in oxygen concentration in the reference gas chamber 49.

Next, an example method for manufacturing the gas sensor 100 will be described hereinafter. First, six unfired ceramic green sheets are prepared, each containing an oxygen-ion-conductive solid electrolyte such as zirconia as the ceramic component. A plurality of sheet holes used for positioning at the time of printing or stacking, a plurality of required through holes, and the like are formed in the green sheets in advance. A space that forms the measurement-object gas flow section is provided in advance in the green sheet for the spacer layer 5 by punching or the like. A space that forms the reference gas chamber 49 is provided in advance in the green sheet for the third substrate layer 3 by punching or the like. Then, the ceramic green sheets are subjected to a pattern printing process and a drying process in accordance with the first substrate layer 1, the second substrate layer 2, the third substrate layer 3, the first solid electrolyte layer 4, the spacer layer 5, and the second solid electrolyte layer 6 to form various patterns on the respective ceramic green sheets. Specifically, the patterns to be formed are patterns for, for example, the respective electrodes described above, leads to be connected to the respective electrodes, the connector electrodes, and the heater unit 70. The pattern printing process is performed by applying pattern-forming paste, which is prepared according to the properties required for the respective objects to be formed, to the green sheets by using a known screen printing technique. The drying process is also performed using a known drying device. Upon completion of pattern printing and drying, an adhesive paste for stacking and bonding the green sheets corresponding to the respective layers is printed and dried. Then, a pressure bonding process is performed. Specifically, the respective green sheets with the adhesive paste formed thereon are positioned by aligning the sheet holes, stacked in a predetermined order, and then subjected to pressure bonding under predetermined temperature and pressure conditions to form a single layered body. The resulting layered body includes a plurality of sensor elements 101. The layered body is cut into the size of the sensor elements 101. Each of the cut pieces of the layered body is fired at a predetermined firing temperature to produce the sensor element 101. The porosity P1 of the lead 38b can be adjusted by, for example, adjusting the proportion of a pore-forming agent in the pattern-forming paste for the lead 38b. Likewise, the porosity P2 of the lead 48b can be adjusted by, for example, adjusting the proportion of a pore-forming agent in the pattern-forming paste for the lead 48b. The porosities of the first reference electrode 42a, the second reference electrode 42b, and the connector electrodes 65b and 65d can also be adjusted by adjusting the proportion of pore-forming agents in the corresponding pattern-forming pastes.

After the sensor element 101 is obtained in the way described above, the sensor assembly 140 (see FIG. 1) with the sensor element 101 built therein is manufactured. The components, such as the protective cover 130 and the rubber stopper 157, are mounted in the sensor assembly 140, and the lead wires 155 are drawn out to the outside from the outer cylinder 148. Then, the control device 90 and the sensor element 101 are connected to each other via the lead wires 155. Thus, the gas sensor 100 is obtained.

The correspondence between the constituent elements of this embodiment and the constituent elements of the present invention will now be clarified. The first substrate layer 1, the second substrate layer 2, the third substrate layer 3, the first solid electrolyte layer 4, the spacer layer 5, and the second solid electrolyte layer 6 of this embodiment correspond to an element body of the present invention, the reference gas chamber 49 corresponds to a reference gas chamber, the reference-gas adjustment pump cell 31 corresponds to a first pump cell, the inner pump electrode 22 corresponds to a first pump electrode, the first reference electrode 42a corresponds to a first reference electrode, the reference gas adjustment pump circuit 37 corresponds to a first pump circuit, the connector electrode 65a corresponds to a first pump electrode terminal, the connector electrode 65b corresponds to a first reference electrode terminal, the lead 38a corresponds to a first pump electrode lead, the lead 38b corresponds to a first reference electrode lead, the measurement pump cell 41 corresponds to a second pump cell, the measurement electrode 44 corresponds to a second pump electrode, the second reference electrode 42b corresponds to a second reference electrode, the measurement pump circuit 47 corresponds to a second pump circuit, the connector electrode 65c corresponds to a second pump electrode terminal, the connector electrode 65d corresponds to a second reference electrode terminal, the lead 48a corresponds to a second pump electrode lead, and the lead 48b corresponds to a second reference electrode lead.

In the gas sensor 100 according to this embodiment described in detail above, since the porous lead 48b is connected to the second porous reference electrode 42b, oxygen in the reference gas chamber 49 can be released to the outside, suppressing an increase in oxygen concentration in the reference gas chamber 49. In addition, setting resistance value R2>resistance value R1 and porosity P2>porosity P1 reduces manufacturing variations for the sensor elements 101, compared with the case where, for example, porosity P2 porosity P1 is satisfied. Therefore, the gas sensor 100 can reduce manufacturing variations while suppressing an increase in oxygen concentration in the reference gas chamber 49.

In addition, by setting the porosity P2 to be greater than or equal to 5%, the effect of suppressing an increase in oxygen concentration in the reference gas chamber 49 is more reliably obtained. By setting the porosity P2 to be less than or equal to 25%, a break in the lead 48b at the time of manufacturing the sensor element 101 can be suppressed.

It goes without saying that the present invention is not limited to the embodiment described above and may be implemented in various forms within the technical scope of the present invention.

In the embodiment described above, the control voltage Vp3 is a constant voltage, although this is not intended to be limiting. For example, the control voltage Vp3 may be a voltage that is repeatedly turned on and off, such as a pulse voltage.

In the embodiment described above, the reference-gas adjustment pump cell 31 has been described as an example of the first pump cell, and the measurement pump cell 41 has been described as an example of the second pump cell. Alternatively, the first and second pump cells may be other pump cells for different uses that are configured to pump oxygen into the reference gas chamber 49. In the embodiment described above, furthermore, the layers 4 to 6 are present between the inner pump electrode 22 and the first reference electrode 42a included in the reference-gas adjustment pump cell 31. Alternatively, it is sufficient that the first pump cell includes one or more solid electrolyte layers between the first pump electrode and the first reference electrode. Likewise, it is sufficient that the second pump cell includes one or more solid electrolyte layers between the second pump electrode and the second reference electrode.

In the embodiment described above, the reference gas is atmospheric air. However, any other gas serving as a reference to detect the concentration of a specific gas in the measurement-object gas may be used. For example, the reference gas chamber 49 or the space 149 may be filled with a gas that is adjusted in advance to have a predetermined oxygen concentration (>oxygen concentration in the measurement-object gas) as a reference gas.

In the embodiment described above, the sensor element 101 is configured to detect the NOx concentration in the measurement-object gas. Alternatively, any other device configured to detect the concentration of a specific gas in the measurement-object gas may be used. For example, any other oxide concentration other than NOx concentration may be detected as a specific gas concentration. When the specific gas is an oxide, as in the embodiment described above, the specific gas itself is reduced in the third internal cavity 61 to produce oxygen. Thus, the measurement pump cell 41 may obtain a detected value (i.e., the pump current Ip2) corresponding to the oxygen to detect the specific gas concentration. Alternatively, the specific gas may be a non-oxide such as ammonia. When the specific gas is a non-oxide, the specific gas is converted to an oxide (e.g., converted to NO in the case of ammonia) such that the converted gas is reduced in the third internal cavity 61 to produce oxygen. The measurement pump cell 41 can obtain a detected value (e.g., the pump current Ip2) corresponding to the oxygen to detect the specific gas concentration. For example, the inner pump electrode 22 in the first internal cavity 20 functions as a catalyst to convert ammonia to NO in the first internal cavity 20.

In the embodiment described above, the element body of the sensor element 101 is a layered body having a plurality of solid electrolyte layers (the layers 1 to 6), although this is not intended to be limiting. It is sufficient that the element body of the sensor element 101 includes at least one oxygen-ion-conductive solid electrolyte layer. For example, the first substrate layer 1 is not a constituent element of any cell and does not need to allow oxygen ions to pass. Thus, the first substrate layer 1 may be a layer composed of a material other than that of a solid electrolyte layer (e.g., a layer composed of alumina).

In the embodiment described above, the pump current Ip1 is used to control the voltage V0 of the main-pump-control oxygen-partial-pressure detection sensor cell 80, although this is not intended to be limiting. For example, feedback control of the pump voltage Vp0 may be performed on the basis of the pump current Ip1 so that the pump current Ip1 becomes the target value Ip1*. That is, the control of the voltage V0 based on the pump current Ip1 may be omitted, and the pump voltage Vp0 may be directly controlled (and therefore the pump current Ip0 may be controlled) on the basis of the pump current Ip1.

Figure 6:
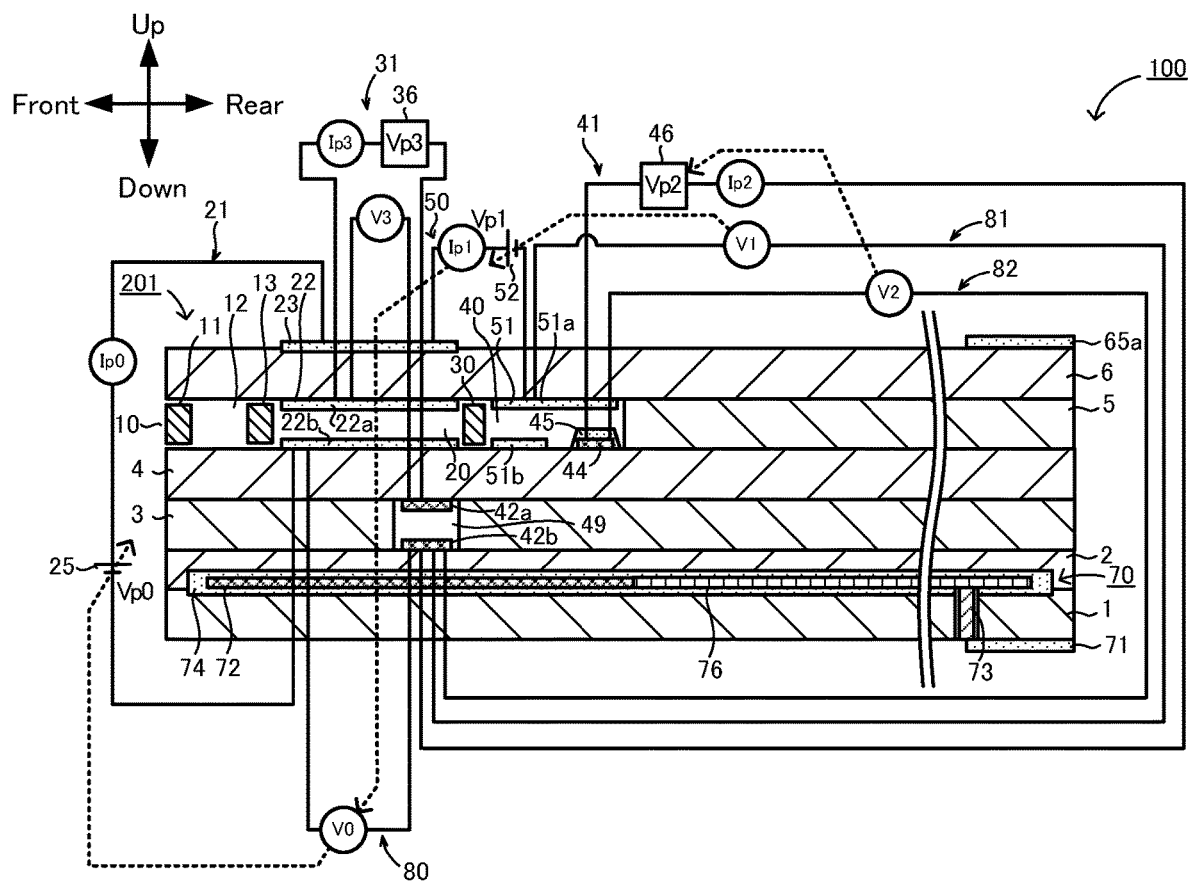
FIG. 6 is a schematic sectional view of a sensor element 201 according to a modification.

In the embodiment described above, the sensor element 101 of the gas sensor 100 includes the first internal cavity 20, the second internal cavity 40, and the third internal cavity 61, although this is not intended to be limiting. For example, as in a sensor element 201 illustrated in FIG. 6, the third internal cavity 61 may not be included. In the sensor element 201 according to a modification illustrated in FIG. 6, the gas inlet 10, the first diffusion control section 11, the buffer space 12, the second diffusion control section 13, the first internal cavity 20, the third diffusion control section 30, and the second internal cavity 40 are formed adjacent to one another in such a manner as to communicate in the stated order between the lower surface of the second solid electrolyte layer 6 and the upper surface of the first solid electrolyte layer 4. The measurement electrode 44 is disposed on the upper surface of the first solid electrolyte layer 4 in the second internal cavity 40. The measurement electrode 44 is covered with a fourth diffusion control section 45. The fourth diffusion control section 45 is a film formed of a porous ceramic body composed of alumina ($Al_2O_3$) or the like. Like the fourth diffusion control section 60 according to the embodiment described above, the fourth diffusion control section 45 serves to limit the amount of NOx flowing into the measurement electrode 44. The fourth diffusion control section 45 also functions as a protective film of the measurement electrode 44. The ceiling electrode portion 51a of the auxiliary pump electrode 51 is formed to extend up to the position immediately above the measurement electrode 44. The sensor element 201 having the configuration described above can also detect the NOx concentration on the basis of the pump current Ip2 in a way similar to that in the embodiment described above. In the sensor element 201 illustrated in FIG. 6, a surrounding portion of the measurement electrode 44 (the inside of the fourth diffusion control section 45) functions as a measurement chamber. That is, the surrounding portion of the measurement electrode 44 implements functions similar to those of the third internal cavity 61.

In the embodiment described above, the gas sensor 100 may not include the control device 90. For example, the gas sensor 100 may include, instead of the control device 90, an external-connection connector attached to the lead wires 155 to connect the control device 90 and the lead wires 155 to each other.

EXAMPLES

The following describes examples indicating specific examples of manufacturing a sensor element. Experimental Examples 1-1 to 6-3, 9-1, and 9-2 correspond to examples of the present invention, and Experimental Examples 7-1 to 8-3 and 9-3 correspond to comparative examples. Note that the present invention is not limited to the following examples.

Experimental Examples 1-1 to 1-3

In Experimental Example 1-1, the sensor element 101 of the gas sensor 100 illustrated in FIGS. 1 and 2 was produced by using the manufacturing method described above. In the production of the sensor element 101, the ceramic green sheets were formed by tape casting of a mixture of zirconia particles containing 4 mol % yttria as a stabilizer with an organic binder, a dispersing agent, a plasticizer, and an organic solvent. The first and second reference electrodes 42a and 42b were porous cermet electrodes composed of Pt and zirconia. The patterns for the first and second reference electrodes 42a and 42b were formed using a paste prepared by mixing a Pt powder, a zirconia powder, a binder, and a pore-forming agent. The leads 38a, 38b, 48a, and 48b and the connector electrodes 65a to 65d were made of Pt. The patterns for these leads were formed using a platinum paste obtained by kneading platinum particles and a solvent. For the leads 38b and 48b and the connector electrodes 65b and 65d, a platinum paste obtained by further kneading the platinum particles and the solvent described above with a pore-forming agent (theobromine) was used. The porosity of the first reference electrode 42a was 10.0%. The porosity of the second reference electrode 42b was 11.5%. The porosity P1 of the lead 38b was 3.0%. The porosity P2 of the lead 48b was 15.0%. The porosity of the connector electrode 65b was 2.5%. The porosity of the connector electrode 65d was 3.1%. The measurement of the porosities was performed by image analysis using the SEM image described above. The resistance value R1 of the reference gas adjustment pump circuit 37 was set to a value obtained by measuring the resistance value between the connector electrodes 65a and 65b by using Versa STAT4 manufactured by Princeton Applied Research in accordance with the AC impedance method in a state where the sensor element 101 was heated to 850° C. by the heater 72. The resistance value R2 of the measurement pump circuit 47 was set to a value obtained by measuring the resistance value between the connector electrodes 65c and 65d in accordance with the same method as that for the resistance value R1. As a result of the measurement, the resistance value R1 was 50.0Ω, the resistance value R2 was 1000.0Ω, and the resistance value R2 was higher than the resistance value R1. Two sensor elements 101 were manufactured under the same manufacturing conditions as those in Experimental Example 1-1 to implement Experimental Examples 1-2 and 1-3. In Experimental Examples 1-2 and 1-3, the values of the porosities P1 and P2 were not exactly the same as those in Experimental Example 1-1. Specifically, in Experimental Example 1-2, the porosity P1 was 2.8%, and the porosity P2 was 17.0%. In Experimental Example 1-3, the porosity P1 was 3.2%, and the porosity P2 was 13.0%. The deviation in the porosities P1 and P2 among Experimental Examples 1-1 to 1-3 is considered to be an inevitable deviation in value due to manufacturing variations among Experimental Examples 1-1 to 1-3. The values of the resistance values R1 and R2 in Experimental Examples 1-2 and 1-3 were not exactly the same as the values in Experimental Example 1-1. Specifically, in Experimental Example 1-2, the resistance value R1 was 53.0Ω, and the resistance value R2 was 1010.0Ω. In Experimental Example 1-3, the resistance value R1 was 47.0Ω, and the resistance value R2 was 990.0Ω. As a result of the measurement of the dimensions of the leads 38b and 48b using the SEM image, in all of Experimental Examples 1-1 to 1-3, the width of the lead 38b was 0.4 mm, the thickness of the lead 38b was 20 μm, the width of the lead 48b was 0.42 mm, and the thickness of the lead 48b was 10 μm.

Experimental Examples 2 to 9

In Experimental Examples 2 to 9, the sensor element 101 was manufactured in the same way as that in Experimental Example 1, except that the proportion of the pore-forming agent in the platinum paste for forming the lead 38b and the lead 48b is changed to variously change the porosities P1 and P2 in the manner as shown in Table 1. In each of Experimental Examples 2 to 9, three sensor elements 101 were produced under the same manufacturing conditions. That is, a total of 24 sensor elements 101 were produced for Experimental Examples 2-1 to 2-3, 3-1 to 3-3, 4-1 to 4-3, 5-1 to 5-3, 6-1 to 6-3, 7-1 to 7-3, 8-1 to 8-3, and 9-1 to 9-3.

[Confirmation of Presence of Break in Lead]

For each of a total of 27 sensor elements 101 in Experimental Examples 1-1 to 9-3, the presence of a break in the leads 38b and 48b was examined. The presence of a break in the lead 38b was confirmed by examining electrical conduction between the connector electrodes 65a and 65b by using a tester. The presence of a break in the lead 48b was confirmed by examining electrical conduction between the connector electrodes 65c and 65d by using the tester. As a result, in all of Experimental Examples 7-1 to 7-3, because of no electrical conduction between the connector electrodes 65c and 65d, a break in the lead 48b was estimated. In all of Experimental Examples 1-1 to 6-3 and 8-1 to 9-3, in contrast, there was no break in the lead 38b or 48b.

[Evaluation of Oxygen Concentration in Reference Gas Chamber]

For each of Experimental Examples 1-1 to 6-3, and 8-1 to 9-3 in which there was no break, the oxygen concentration in the reference gas chamber 49 during use of the sensor element 101 was evaluated. Specifically, first, in Experimental Example 1-1, the sensor element 101 was incorporated into the gas sensor 100 illustrated in FIGS. 1 to 3, and the gas sensor 100 was attached to the pipe 190. A model gas in which the base gas was nitrogen and the NOx concentration was 1500 ppm was caused to flow through the pipe 190. In this state, the control of the pump cells 21, 41, and 50 and the heater power supply 78 described above by the control device 90, the acquisition of the voltages V0, V1, and V2 from the sensor cells 80 to 82 described above, and the measurement of the resistance value of the reference-gas adjustment pump cell 31 were continuously performed. The target value of the temperature of the first solid electrolyte layer 4 to be calculated on the basis of resistance value of the reference-gas adjustment pump cell 31 was set to 850° C. Further, the control unit 91 controlled the power supply circuit 36 so as to apply the small voltage Vp3 only for the measurement of the resistance value of the reference-gas adjustment pump cell 31 to prevent the reference-gas adjustment pump cell 31 from pumping oxygen into the reference gas chamber 49. Accordingly, the pumping of oxygen into the reference gas chamber 49 is basically performed only by the flow of the pump current Ip2. The state of causing the model gas to flow through the pipe 190 and the state of controlling the sensor element 101 by the control device 90 were maintained for 20 minutes, and a voltage (referred to as a voltage Vref) between the outer pump electrode 23 and the first reference electrode 42a for this duration was measured. The measurement of the voltage Vref was performed at a timing other than the time of measurement of the resistance value of the reference-gas adjustment pump cell 31 (the time of application of the voltage Vp3). The voltage Vref during no application of the voltage Vp3 has a value based on the oxygen concentration difference between the surrounding of the outer pump electrode 23 and the surrounding of the first reference electrode 42a, and the value of the voltage Vref increases as the oxygen concentration difference increases. The oxygen concentration of the model gas, that is, the oxygen concentration around the outer pump electrode 23, is constant (the value is 0%). Thus, the value of the voltage Vref increases as the oxygen concentration of the first reference electrode 42a increases. The measurement of the voltage Vref was repeatedly performed during 20 minutes. When the measured voltage Vref fell within a predetermined range (greater than or equal to 80% and less than or equal to 120%) even after the elapse of 20 minutes, with 100% representing the value of the voltage Vref at the start of the measurement, the increase in oxygen concentration in the reference gas chamber 49 was determined to be sufficiently suppressed ("A"). When the measured voltage Vref fell within the predetermined range until the elapse of 15 minutes but exceeded the upper limit of the predetermined range before the elapse of 20 minutes, the increase in oxygen concentration in the reference gas chamber 49 was determined to be suppressed to some extent ("B"). When the measured voltage Vref exceeded the upper limit of the predetermined range before the elapse of 15 minutes, the increase in oxygen concentration in the reference gas chamber 49 was determined to be insufficiently suppressed ("F"). Similar measurement and evaluation were performed for Experimental Examples 1-2 to 6-3 and 8-1 to 9-3. In Experimental Examples 1-1 to 6-3 and 8-1 to 9-3, the voltage Vref did not fall below the lower limit (80%) of the predetermined range during 20 minutes. The results of the evaluation described above are shown in Table 1.

[Calculation of Coefficients of Variation of Resistance Values R1 and R2]

For the three sensor elements 101 in Experimental Examples 1-1 to 1-3, coefficients of variation were calculated as values indicating variations in the resistance values R1 and R2 described above. In Experimental Example 1, the coefficient of variation of the resistance value R1 was 0.049, and the coefficient of variation of the resistance value R2 was 0.008. Likewise, the resistance values R1 and R2 were measured for the three sensor elements 101 in Experimental Examples 8-1 to 8-3, and coefficients of variation were calculated as values indicating variations in the resistance values R1 and R2. In Experimental Example 8, the coefficient of variation of the resistance value R1 was 0.148, and the coefficient of variation of the resistance value R2 was 0.003. The resistance values R1 and R2 and the values of the coefficients of variation for Experimental Examples 1 and 8 are shown in Table 1. Although not shown in Table 1, the value of the resistance value R2 was higher than the value of the resistance value R1 for all of Experimental Examples 2-1 to 6-3 and 9-1 to 9-3 other than Experimental Examples 7-1 to 7-3 in which the resistance value R2 could not be measured due to the presence of a break.

TABLE 1

| | Porosity P1 of the first reference electrode lead (lead 38b) [%] | Porosity P2 of the second reference electrode lead (lead 48b) [%] | Evaluation of oxygen concentration in reference gas chamber | Presence of break in lead | R1 [Ω] | R2 [Ω] | Coefficient of variation of R1 | Coefficient of variation of R2 |
|---|---|---|---|---|---|---|---|---|
| Experimental Example 1-1 | 3.0 | 15.0 | A | No | 50.0 | 1000.0 | 0.049 | 0.008 |
| Experimental Example 1-2 | 2.8 | 17.0 | A | No | 53.0 | 1010.0 | | |
| Experimental Example 1-3 | 3.2 | 13.0 | A | No | 47.0 | 990.0 | | |
| Experimental Example 2-1 | 1.0 | 16.0 | A | No | — | — | — | — |
| Experimental Example 2-2 | 1.3 | 20.0 | A | No | — | — | — | — |
| Experimental Example 2-3 | 1.2 | 17.5 | A | No | — | — | — | — |
| Experimental Example 3-1 | 2.8 | 10.0 | A | No | — | — | — | — |
| Experimental Example 3-2 | 2.6 | 11.8 | A | No | — | — | — | — |
| Experimental Example 3-3 | 3.0 | 12.3 | A | No | — | — | — | — |
| Experimental Example 4-1 | 5.0 | 16.7 | A | No | — | — | — | — |
| Experimental Example 4-2 | 4.8 | 14.7 | A | No | — | — | — | — |
| Experimental Example 4-3 | 4.5 | 19.0 | A | No | — | — | — | — |
| Experimental Example 5-1 | 1.9 | 25.0 | A | No | — | — | — | — |
| Experimental Example 5-2 | 2.0 | 20.0 | A | No | — | — | — | — |
| Experimental Example 5-3 | 1.8 | 18.6 | A | No | — | — | — | — |
| Experimental Example 6-1 | 3.6 | 8.6 | B | No | — | — | — | — |
| Experimental Example 6-2 | 3.9 | 9.0 | B | No | — | — | — | — |
| Experimental Example 6-3 | 3.4 | 7.9 | B | No | — | — | — | — |
| Experimental Example 7-1 | 4.1 | 29.4 | — | Presence | — | — | — | — |
| Experimental Example 7-2 | 4.6 | 35.3 | — | Presence | — | — | — | — |
| Experimental Example 7-3 | 3.7 | 45.0 | — | Presence | — | — | — | — |
| Experimental Example 8-1 | 15.3 | 3.1 | A | No | 55.0 | 1000.0 | 0.148 | 0.003 |
| Experimental Example 8-2 | 16.8 | 2.8 | A | No | 65.0 | 1005.0 | | |
| Experimental Example 8-3 | 12.5 | 3.5 | A | No | 45.0 | 997.0 | | |
| Experimental Example 9-1 | 3.1 | 5.0 | B | No | — | — | — | — |
| Experimental Example 9-2 | 2.7 | 3.5 | F | No | — | — | — | — |
| Experimental Example 9-3 | 3.3 | 2.0 | F | No | — | — | — | — |

As shown in Table 1, when Experimental Example 1 in which the porosity P2 is higher than the porosity P1 is compared with Experimental Example 8 in which the porosity P1 is higher than the porosity P2, the value of the coefficient of variation of the resistance value R1 in Experimental Example 8 is larger than the coefficients of variation of the resistance values R1 and R2 in Experimental Example 1. It was therefore confirmed that setting the porosity P2 of the lead 48b included in the measurement pump circuit 47 having a higher resistance value among the reference gas adjustment pump circuit 37 and the measurement pump circuit 47 to be higher than the porosity P1 of the lead 38b included in the reference gas adjustment pump circuit 37 having a lower resistance value can reduce manufacturing variations for the sensor elements 101. As described above, the higher the porosity of a lead, the more likely it is that the resistance value of the lead varies due to a manufacturing error. In Experimental Example 8, since the porosity P1 of the lead 38b is higher than the porosity P2 of the lead 48b, it is considered that the variation in the resistance value of the lead 38b is larger than the variation in the resistance value of the lead 48b, and that due to the influence of the variations, the resistance value R1 of the reference gas adjustment pump circuit 37 including the lead 38b varies largely. In Experimental Example 1, in contrast, since the porosity P2 of the lead 48b is higher than the porosity P1 of the lead 38b, it is considered that the variation in the resistance value of the lead 48b is larger than the variation in the resistance value of the lead 38b; however, the resistance value R2 is larger than the resistance value R1, and thus even the variation in the resistance value of the lead 48b may less affect the variation in the resistance value R2, resulting in a small variation in the resistance value R2.

As shown in Table 1, furthermore, it was confirmed that as the value of at least one of the porosities P1 and P2 increased, the effect of suppressing an increase in oxygen concentration in the reference gas chamber 49 increased. Specifically, in Experimental Examples 9-2 and 9-3 in which both the porosities P1 and P2 were less than 5%, the evaluation of the oxygen concentration in the reference gas chamber 49 was "F", whereas in Experimental Examples 1-1 to 6-3, 8-1 to 8-3, and 9-1 in which one of the porosities P1 and P2 was greater than or equal to 5%, the evaluation was "B" or higher. In Experimental Examples 1-1 to 5-3 and 8-1 to 8-3 in which one of the porosities P1 and P2 was greater than or equal to 10%, the evaluation was "A". However, if the porosity P1 is increased, the increase in oxygen concentration in the reference gas chamber 49 can be suppressed, but, as described above, the manufacturing variations for the sensor elements 101 are increased. In contrast, it was confirmed that increasing the porosity P2 without increasing the porosity P1 could reduce manufacturing variation while suppressing an increase in oxygen concentration in the reference gas chamber 49. In particular, from the viewpoint of suppressing an increase in oxygen concentration in the reference gas chamber 49, it is considered that the porosity P2 is preferably greater than or equal to 5%, and more preferably greater than or equal to 10%. In addition, from the results of Experimental Examples 7-1 to 7-3, it is considered that the porosity P2 is preferably less than or equal to 25% to suppress a break in the lead 48b at the manufacturing time.

What is claimed is:

1. A sensor element for detecting a specific gas concentration in a measurement-object gas, the sensor element comprising:
   an element body including an oxygen-ion-conductive solid electrolyte layer and having formed therein a measurement-object gas flow section and a reference gas chamber, the measurement-object gas flow section being a section into and through which the measurement-object gas is introduced and flows, the reference gas chamber being a chamber in which a reference gas used as a reference to detect the specific gas concentration in the measurement-object gas is to be stored;
   a first pump cell including a first pump electrode disposed in a portion of the element body that comes into contact with the measurement-object gas, and a first reference electrode that is porous and disposed in the reference gas chamber, the first pump cell being configured to pump oxygen into around the first reference electrode from around the first pump electrode;
   a first pump circuit including the first pump cell, a first pump electrode terminal disposed on an outer side of the element body, a first reference electrode terminal disposed on the outer side of the element body, a first pump electrode lead that connects the first pump electrode terminal and the first pump electrode to each other, and a first reference electrode lead that connects the first reference electrode terminal and the first reference electrode to each other;
   a second pump cell including a second pump electrode disposed in a portion of the element body that comes into contact with the measurement-object gas, and a second reference electrode that is porous and disposed in the reference gas chamber, the second pump cell being configured to pump oxygen into around the second reference electrode from around the second pump electrode; and
   a second pump circuit including the second pump cell, a second pump electrode terminal disposed on the outer side of the element body, a second reference electrode terminal disposed on the outer side of the element body, a second pump electrode lead that connects the second pump electrode terminal and the second pump electrode to each other, and a second reference electrode lead that connects the second reference electrode terminal and the second reference electrode to each other, wherein
   a resistance value R2 between the second pump electrode terminal and the second reference electrode terminal of the second pump circuit is higher than a resistance value R1 between the first pump electrode terminal and the first reference electrode terminal of the first pump circuit in a temperature range greater than or equal to 700° C. and less than or equal to 900° C., and
   a porosity P2 of the second reference electrode lead is higher than a porosity P1 of the first reference electrode lead.

2. The sensor element according to claim 1, wherein the porosity P2 is greater than or equal to 5% and less than or equal to 25%.

3. The sensor element according to claim 1, wherein the porosity P1 is greater than or equal to 1% and less than or equal to 5%.

4. A gas sensor comprising the sensor element according to claim 1.

* * * * *